United States Patent
Jiang et al.

(10) Patent No.: US 10,083,508 B2
(45) Date of Patent: Sep. 25, 2018

(54) METHOD AND SYSTEM FOR ANALYZING WOUND STATUS

(71) Applicant: INDUSTRIAL TECHNOLOGY RESEARCH INSTITUTE, Hsinchu (TW)

(72) Inventors: Yue-Min Jiang, New Taipei (TW); Ho-Hsin Lee, Hsinchu (TW); Yi-Fei Luo, Hsinchu County (TW); I-Ju Yeh, Hsinchu (TW); Li-Ying Wu, Hsinchu (TW)

(73) Assignee: INDUSTRIAL TECHNOLOGY RESEARCH INSTITUTE, Hsinchu (TW)

(*) Notice: Subject to any disclaimer, the term of this patent is extended or adjusted under 35 U.S.C. 154(b) by 0 days.

(21) Appl. No.: 15/625,632

(22) Filed: Jun. 16, 2017

(65) Prior Publication Data

US 2018/0197291 A1  Jul. 12, 2018

(30) Foreign Application Priority Data

Jan. 12, 2017 (TW) .............................. 106101003 A (51) Int. Cl.
*G06T 7/00* (2017.01)
*A61B 5/00* (2006.01)
(Continued)

(52) U.S. Cl.
CPC .......... *G06T 7/0016* (2013.01); *A61B 5/0015* (2013.01); *A61B 5/0064* (2013.01);
(Continued)

(58) Field of Classification Search
CPC .......... G06T 7/0016; G06T 7/163; G06T 7/55
See application file for complete search history.

(56) References Cited

U.S. PATENT DOCUMENTS

| 5,503,559 A | 4/1996 | Vari |
| 8,013,304 B2 | 9/2011 | Haigh et al. |

(Continued)

FOREIGN PATENT DOCUMENTS

| CN | 1555273 A | 12/2004 |
| TW | 200613733 A | 5/2006 |

(Continued)

OTHER PUBLICATIONS

Chang, Chih et al. "Robust Dermatological Wound Image Segmentation in Clinical Photos" The 5th IEEE International Conference on E-Health and Bioengineering—EHB, Nov. 19-21, 2015, 4 pages.

(Continued)

*Primary Examiner* — Hugh H Maupin
(74) *Attorney, Agent, or Firm* — Birch, Stewart, Kolasch & Birch, LLP (57) ABSTRACT

A system for analyzing wound status is provided. The system includes an image obtaining device and an image analyzing device. The image obtaining device is configured to obtain a plurality of infrared (IR) images which are photographed from a wound of a user's body portion, wherein the plurality of IR images are photographed at different time. The image analyzing device is configured to align the plurality of IR images based on features of non-wound regions from the plurality of IR images, and then analyze wound image regions from the plurality of IR images for finding out variations of the wound.

15 Claims, 5 Drawing Sheets

(51) Int. Cl.
    *G06E 1/02*    (2006.01)
    *G06T 7/13*    (2017.01)
    *G06T 7/162*   (2017.01)
    *G06T 7/11*    (2017.01)
    *G06T 7/174*   (2017.01)
    *G06T 7/55*    (2017.01)
    *G06T 7/70*    (2017.01)
(52) U.S. Cl.
    CPC .......... *A61B 5/0075* (2013.01); *A61B 5/0086* (2013.01); *G06E 1/02* (2013.01); *G06T 7/11* (2017.01); *G06T 7/13* (2017.01); *G06T 7/162* (2017.01); *G06T 7/174* (2017.01); *G06T 7/55* (2017.01); *G06T 7/70* (2017.01); *G06T 7/97* (2017.01)

(56) References Cited

U.S. PATENT DOCUMENTS

| 9,042,967 | B2 | 5/2015 | Dacosta et al. |
| 2010/0041998 | A1 | 2/2010 | Postel |
| 2010/0172567 | A1* | 7/2010 | Prokoski ............... A61B 5/0064 382/132 |
| 2013/0116573 | A1 | 5/2013 | Herman |
| 2015/0011892 | A1* | 1/2015 | Sostek ................. A61B 5/0064 600/473 |

FOREIGN PATENT DOCUMENTS

| TW | 200806245 A | 2/2008 |
| TW | 201202197 A1 | 1/2012 |
| TW | 201509373 A | 3/2015 |
| TW | I519274 B | 2/2016 |

OTHER PUBLICATIONS

Wang, Changhan et al. "A Unified Framework for Automatic Wound Segmentation and Analysis with Deep Convolutional Neural Networks" IEEE, 2015, pp. 2415-2418.

Taiwanese Office Action and Search Report for Taiwanese Application No. 106101003, dated Jul. 20, 2017.

* cited by examiner

METHOD AND SYSTEM FOR ANALYZING WOUND STATUS

CROSS-REFERENCE TO RELATED APPLICATION

The present application is based on, and claims priority from, Taiwan Application Serial Number 106101003, filed on Jan. 12, 2017, the disclosure of which is hereby incorporated by reference herein in its entirety.

TECHNICAL FIELD

The disclosure relates to a method and system for analyzing wound status.

BACKGROUND

Patients stayed in hospital may have several kinds of wounds, such as accident burn/scald (burn or scald) wounds, surgical wounds, pressure ulcers and so on. Traditionally and generically, nurses assess and treat patients with wounds through eye observation, and record wound status in text. Currently, wound status assessing is performed by using a portable card of pressure ulcers classification to assist nurses in wound classification by eye observation.

However, distorted assessment may arise by eye observing and text recordings of wound variations may also get distortion due to difference of subjective consciousness between nurses. Therefore, an assistive tool for observing wound variations is needed so as to provide records objectively, to save communication time between nursing persons and further to upgrade quality of nursing care.

SUMMARY

According to an embodiment of the present disclosure, a system for analyzing wound status is provided. The system includes an image obtaining device and an image analyzing device. The image obtaining device is configured to obtain a plurality of infrared (IR) images which are photographed from a wound of a user's body portion, wherein the plurality of IR images include a first IR image photographed at a first time and a second IR image photographed at a second time, the first IR image includes a first pattern image of vascular distribution of the user's body portion and the second IR image includes a second pattern image of vascular distribution of the user's body portion. The image analyzing device, coupled to the image obtaining device, includes a wound detecting module, an image calibrating module and a wound analyzing module. The wound detecting module is configured to detect a first wound image region from the first IR image, and detects a second wound image region from the second IR image. The image calibrating module is configured to respectively recognize a non-wound region from the first IR image and a non-wound region from the second IR image to obtain a first feature group and a second feature group, produce calibration information according to the first feature group and the second feature group, and utilize the calibration information for aligning the second IR image to the first IR image to produce a calibrated image. The wound analyzing module is configured to recognize a third wound image region from the calibrated image and make comparison between the third wound image region and the first wound image region for finding out variations of the wound.

According to another embodiment of the present disclosure, a method for analyzing wound status is provided. The method comprises obtaining a plurality of infrared (IR) images which are photographed from a wound of a user's body portion, wherein the plurality of IR images include a first IR image photographed at a first time and a second IR image photographed at a second time, the first IR image includes a first pattern image of vascular distribution of the user's body portion and the second IR image includes a second pattern image of vascular distribution of the user's body portion; detecting a first wound image region and a second wound image region from the first IR image and the second IR image respectively; recognizing a first non-wound region from the first IR image and a second non-wound region from the second IR image to obtain a first feature group and a second feature group, respectively; producing calibration information according to the first feature group and the second feature group; and utilizing the calibration information for aligning the second IR image to the first IR image to produce a calibrated image; and recognizing a third wound image region from the calibrated image and comparing the third wound image region with the first wound image region for finding out status variations of the wound.

DETAILED DESCRIPTION OF DISCLOSED EMBODIMENTS

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 1:
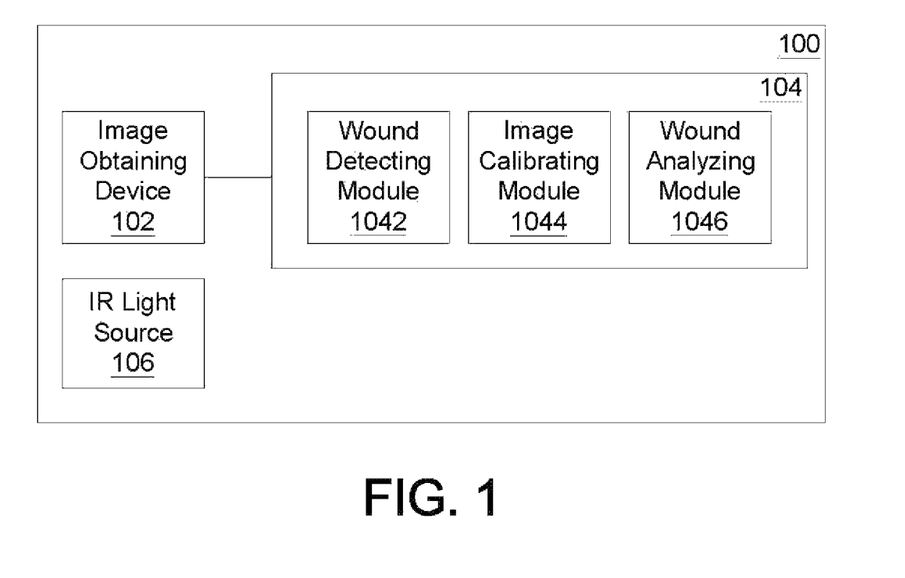
FIG. 1 is a block diagram of a system for analyzing wound status according to an embodiment.

FIG. 1 is a block diagram of a system 100 for analyzing wound status according to an embodiment. The system 100 may include an image obtaining device 102 and an image analyzing device 104.

The image obtaining device 102 may be an electronic device having functionality of IR image capturing, such as an IR camera. The image obtaining device 102 may photograph a target for capturing an IR image of the target. The target may be a user's body portion having wound to be observed. Since subcutaneous blood vessels can be captured under IR lighting, the IR image of the user's body portion can include a pattern image of vascular distribution.

The image obtaining device 102 may also be an image transmission interface or an Input/Output (I/O) electric circuit for obtaining images captured by a camera and transmitting the images to the image analyzing device 104.

The image analyzing device 104 may couple to the image obtaining device 102 and include a wound detecting module 1042, an image calibrating module 1044 and a wound analyzing module 1046.

The image analyzing device 104 may be implemented by a computing system including a central processing unit (CPU), a microprocessor, application-specific integrated circuit (ASIC), or any electric/optical circuits which are capable of data processing or data computing. The wound detecting module 1042, the image calibrating module 1044 and/or the wound analyzing module 1046 may be implemented through hardware (for example, electric circuits), software (for example, program instructions) or combination thereof.

The image analyzing device 104 may obtain status variations of wound (for example, area variations of wound) of a user's body portion through executing series of analyses on plural IR images of the user's body portion which are captured at different time; the series of analyses may include wound region detection, vascular distribution recognition, and image alignment. In an embodiment, the status variations of wound may be revealed to a Graphical User Interface (GUI) via texts, graphs or combination thereof.

The system 100 for analyzing wound status may include an IR light source 106. The IR light source 106 may project IR light to a user's body portion having wound so as to enhance visibility of subcutaneous blood vessels. For instance, when the wound locates at a body portion having thicker adipose layer (for example, buttocks), light solely provided from the image obtaining device 102 may not be intense for capturing obvious IR image of vascular distribution in the user's body portion, therefore IR light may be applied to enhance visibility of subcutaneous blood vessels in such case. In an embodiment, wavelength of the IR light source 106 may be located within a range from 500 nm to 1300 nm.

Figure 2:
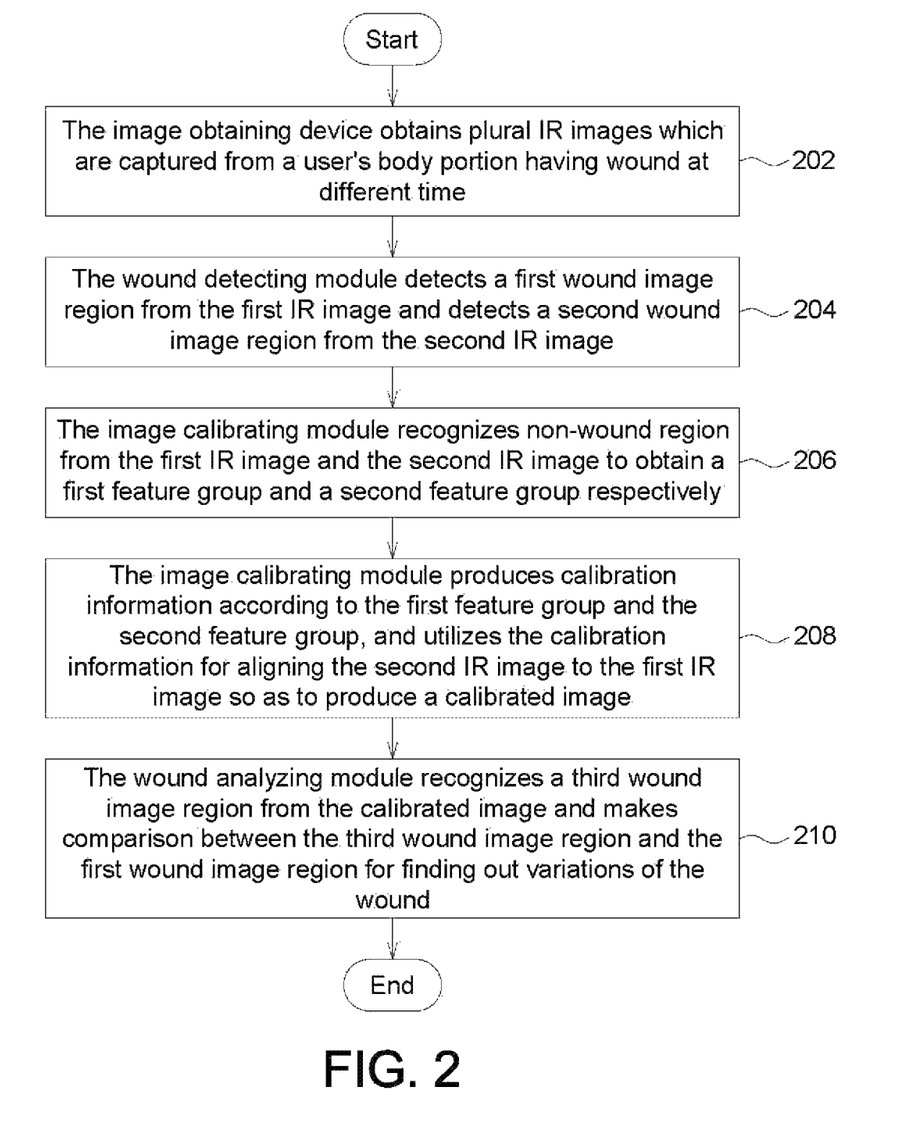
FIG. 2 is a flow chart of a method for analyzing wound status according to an embodiment.

FIG. 2 is a flow chart of a method for analyzing wound status according to an embodiment. The method may be implemented by the system 100 of FIG. 1.

In Step 202, the image obtaining device 102 may obtain plural IR images which are captured from a user's body portion having wound at different time.

The aforesaid plural IR images may include a first IR image captured from the user's body portion at a first time and a second IR image captured from the user's body portion at a second time. Due to visibility enhancement of subcutaneous blood vessels by IR light treatment, the first IR image and the second IR image may include a first pattern image of vascular distribution and a second pattern image of the vascular distribution respectively.

In an embodiment, one of the plural images (such as, the first IR image) may be treated as a reference image, and other/others of the plural images (such as, the second IR image) may be aligned to the reference image so as to facilitate the comparison of the pattern images of vascular distribution in the plural images captured at different time.

In an embodiment, the first IR image, which is treated as reference image, may be a Top-View IR image captured by an IR camera from a top of a wound region. Capturing order of the reference image and the other IR image is not limited in the present disclosure. For example, the first time for capturing the first IR image may be posterior or prior to the second time for capturing the second IR image.

In Step 204, the wound detecting module 1042 may detect a first wound image region from the first IR image and detect a second wound image region from the second IR image.

Generally, phases of wound healing may include inflammatory phase, proliferative phase and mature synovitis phase, and temperature variations of wound may accompany with phase variations of wound healing. For IR image, different temperatures may correspond to different feature values, such as gray scale, brightness of pixels. Therefore, the wound detecting module 1042 may figure out a complete boundary of a wound image region by detecting variations of feature values between the wound image region and surroundings thereof.

In an embodiment, the wound detecting module 1042 may perform a Thresholding process (for example, Watershed Thresholding process) and/or an Edge-Detecting process on the first IR image and the second IR image so as to respectively detect the first wound image region from the first IR image and the second wound image region from the second IR image.

In an embodiment, the wound detecting module 1042 may perform image enhancement process on the IR images to enhance pattern images of vascular distribution in the IR images. The image enhancement process may include brightness averaging algorithm, edge sharpening algorithm and the likes of Computer Graphics algorithms.

In Step 206, the image calibrating module 1044 may respectively recognize non-wound region from the first IR image and the second IR image to obtain a first feature group and a second feature group.

In an embodiment, the first feature group and second feature group may be obtained by performing image feature extraction algorithms, such as Scale Invariant Feature Transform (SIFT), Speeded-Up Robust Features (SURF).

The first feature group may include at least one feature point of a vascular distribution included in the first pattern image of vascular distribution, and the second feature group may include at least one feature point of a vascular distribution included in the second pattern image of vascular distribution. In an embodiment, the image calibrating module 1044 may obtain vascular positions and connecting attitudes from those pattern images of vascular distribution by performing Computer Graphics algorithms, such as edge detecting and gradient detecting for adjacent edges, on those pattern images and may extract features of vascular distribution by filtering out unrepresentative features.

Vascular distribution, located at non-wound region, do not vary obviously as time goes by, hence the first feature group and the second feature group may be treated as reference for aligning the second IR image to the first IR image.

In Step 208, the image calibrating module 1044 may produce calibration information according to the first feature group and the second feature group, and utilizes the calibration information for aligning the second IR image to the first IR image so as to produce a calibrated image.

For example, if plural first feature points included in the first feature group are one to one corresponding to plural second feature points included in the second feature group, the image calibrating module 1044 may analyze a skew between a principle axis of a first region and a principle axis of a second region to produce the calibration information, wherein the first region (such as maximum visible region) is an image region covering the plural first feature points and the second region (such as maximum visible region) is an image region covering the plural second feature points, and then image calibrating module 1044 may align the principle axis of the second region to the principle axis of the first region so as to transform the second IR image to the calibrated image.

In an embodiment, the image calibrating module 1044, based on SIFT algorithm or SURF algorithm, may find out those one to one corresponding feature points from different IR images. Then, the image calibrating module 1044 may calculate a corresponding matrix (for example, Hessian Matrix) based on the coordinates of those feature points, the corresponding matrix may be a block matrix constituted of second order partial derivatives which preform corresponding relation of multivariate physical coordinates.

With calculation for the corresponding matrix, the image calibrating module 1044 may calculate a corresponding principle axis in relation to rotation and zoom between two IR images and may calibrate principle axes of the IR images to a common orientation by mapping transformation (for example, Affine transformation) for completing image alignment, so that the calibrated one or more IR images may have the same angle of view as the reference image has.

In Step 210, the wound analyzing module 1046 may recognize a third wound image region from the calibrated image and make comparison between the third wound image region and the first wound image region for finding out variations of the wound.

With Time-of-Flight (TOF) distance measurement theory for a kind of IR camera, the wound analyzing module 1046 may analyze difference among feature values of pixels in an IR image (for example, difference among brightness of pixels) to calculate a distance between any two pixels in the IR image, and further to calculate a physical distance between coordinates of two points based on triangulation distance measurement. Therefore, a proportional scale may be built by capturing a Top-View IR image of the wound. The proportional scale may be treated as a basic standard for calculating the real world distance dimensions of other IR images captured at another time.

In an embodiment, the wound analyzing module 1046 may calculate differences among feature values of pixels in the first IR image so as to figure out an area size of the first wound image region, and then may treat the first wound image region as a basic standard and compare the first wound image region with the third wound image region for calculating an area size of the third wound image region.

Figure 3:
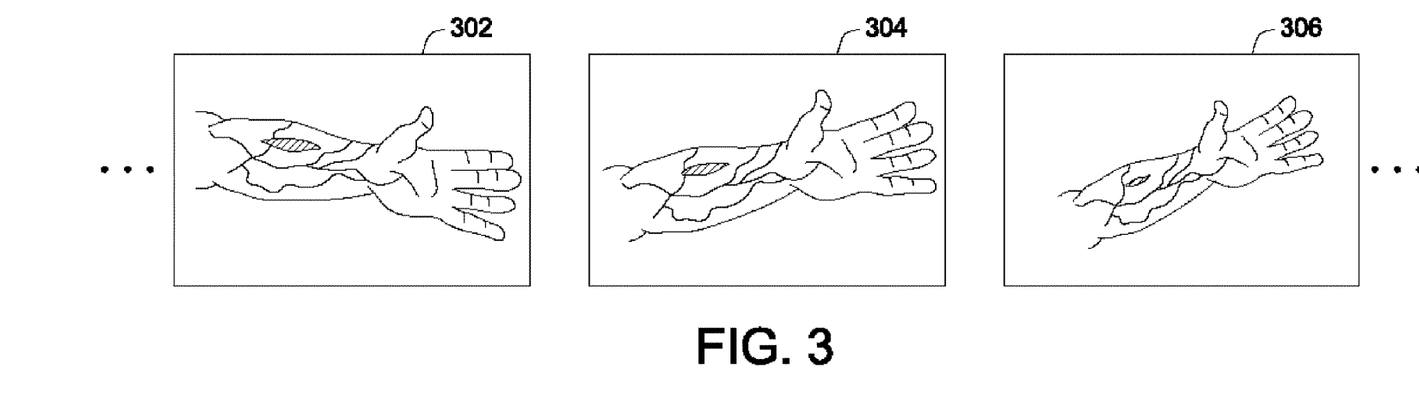
FIG. 3 is a schematic view of plural IR images provided from an image obtaining device according to an embodiment.

FIG. 3 is a schematic view of plural IR images provided from an image obtaining device 102 according to an embodiment. Referring to FIG. 3, the image obtaining device 102 may photograph a wound region (shown as slashed-line region) of an arm for sequentially capturing IR images 302, 304 and 306. The arm is photographed under IR lighting circumstances, hence each arm image of the IR images 302, 304 and 306 includes pattern image of vascular distribution (shown as bold curves).

If the IR image 302 is treated as a reference image (such as the first IR image), the image analyzing device 104 may align the other IR images 304, 306 to the IR image 302 for comparing wound image regions, but the scope of the disclosure is not limited thereto. In the same way, if the IR image 304 is treated as a reference image, the image analyzing device 104 may align the other IR images 302, 306 to the IR image 304 for comparing wound image regions, and so on. In an embodiment, a Top-View captured IR image of the wound region may be treated as a reference image.

Figure 4:
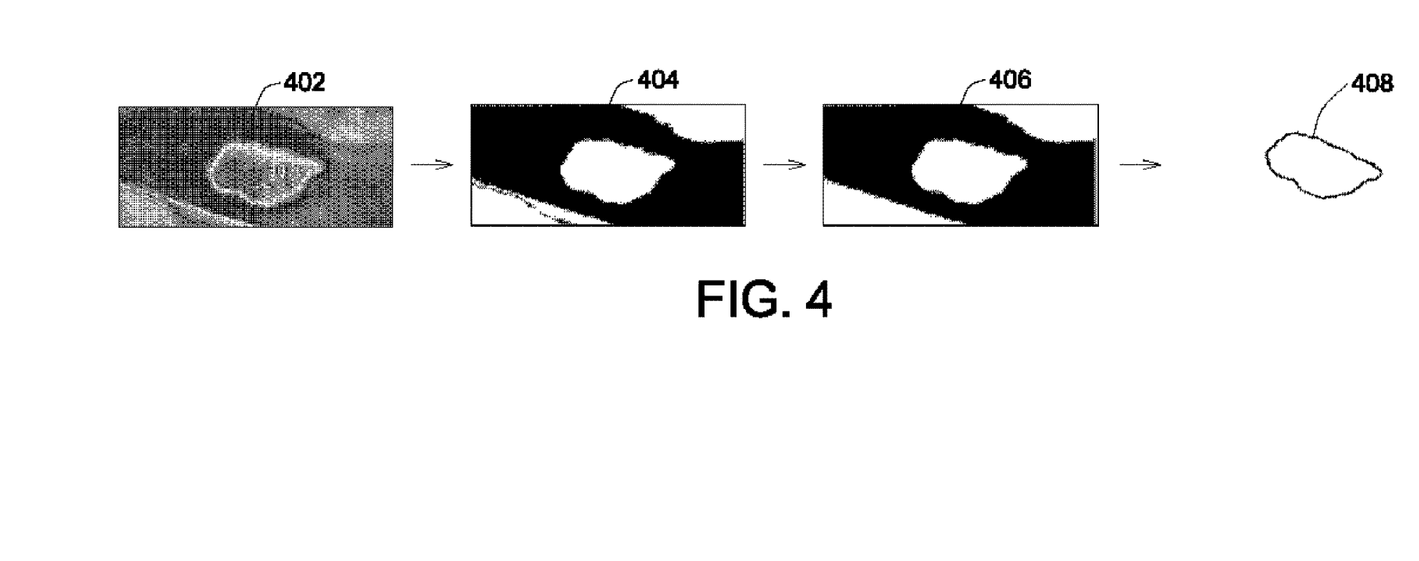
FIG. 4 is a schematic view of a wound image region recognized by a wound detecting module according to an embodiment.

FIG. 4 is a schematic view of a wound image region recognized by a wound detecting module 1042 according to an embodiment. Referring to FIG. 4, firstly, the wound detecting module 1042 may perform thresholding process to the IR image 402 so as to figure out wound region (shown as white region of the arm image in the image 404) and non-wound region (shown as black region of the arm image in the image 404).

Next, the wound detecting module 1042 may perform edge detecting and noise filtering to the image 404 so as to produce an image 406, and a wound region 408 may be extracted from the image 406. Then, the wound detecting module 1042 may mark the wound image region 408 for excluding the wound image region 408 in the following image processing steps (for example, steps of feature extracting from images of vascular distribution.).

Figure 5:
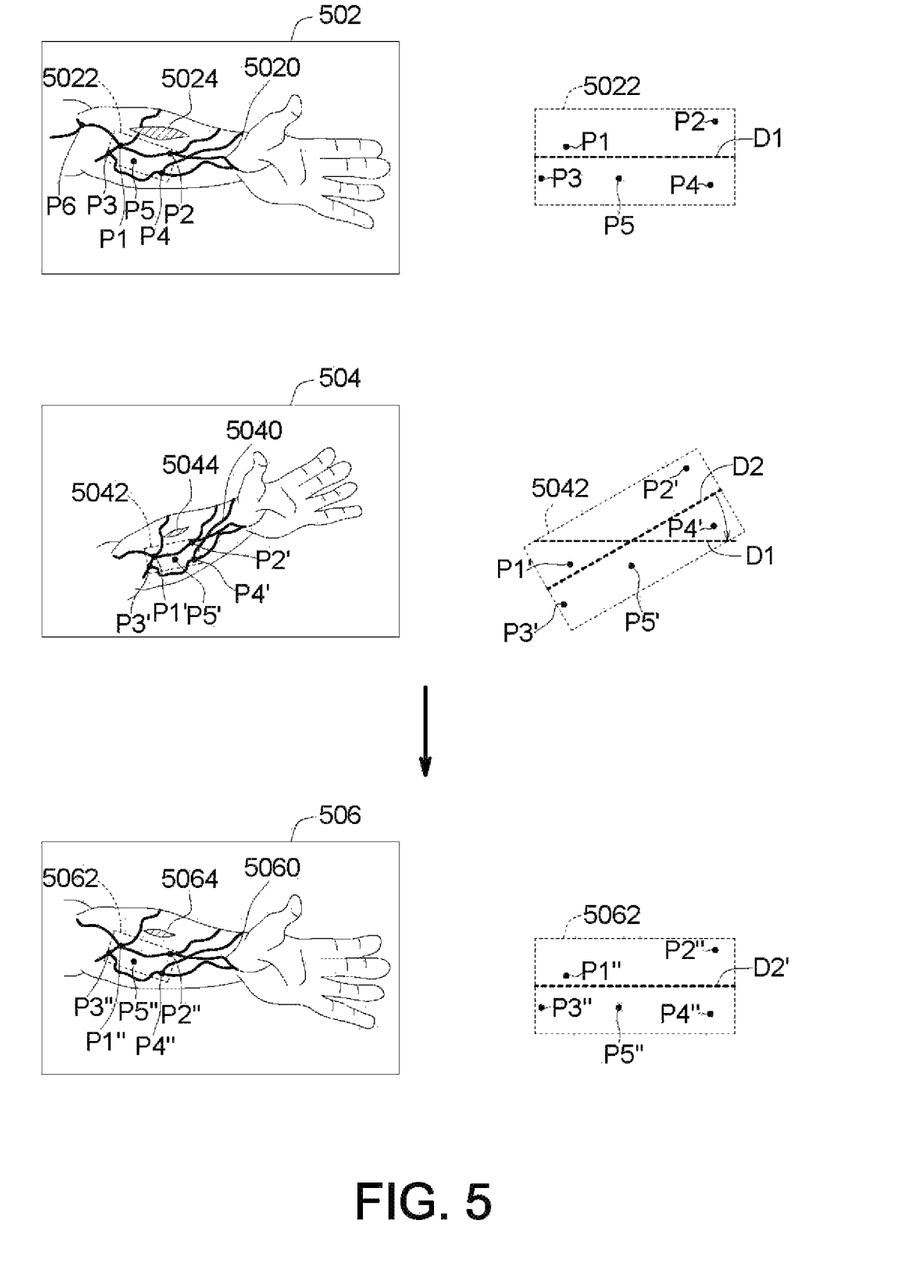
FIG. 5 is a schematic view of aligning plural IR images by an image calibrating module to an embodiment.

FIG. 5 is a schematic view of aligning plural IR images by an image calibrating module 1044 according to an embodiment. Referring to FIG. 5, an IR image 502 (such as the first IR image) may be treated as a reference image, the image calibrating module 1044 may align an IR image 504 (such as the second IR image) to the IR image 502 so as to produce an IR image 506 (such as the calibrated image).

The IR image 502 includes a pattern image of vascular distribution 5020 (such as the first pattern image of vascular distribution) and a wound image region 5024 (such as the first wound image region) corresponding with the wound region of the arm.

In the embodiment, the image calibrating module 1044 finds one or more feature points P1-P6 (such as the foresaid first feature group) out from the IR image 502. Among the feature points P1-P6, one or more feature points (such as feature points P1-P4) are extracted from the pattern image of vascular distribution 5020.

Different from the IR image 502, the IR image 504 is captured at another time (prior or later), and the IR image 504 also includes pattern image of vascular distribution 5040 (such as the second pattern image of vascular distribution) and wound image region 5044 (such as the second wound image region) corresponding to the wound region of the arm.

The image calibrating module 1044 finds one or more feature points P1'-P5' (such as the foresaid second feature group) out from the IR image 504. Among the feature points P1'-P5', at least one or more feature points (such as feature points P1'-P4') are extracted from the pattern image of vascular distribution 5040.

As aforementioned, the image calibrating module 1044, based on several matching method, such as the SURF or SIFT algorithm, may find out the corresponding feature points among the IR image 502 and the IR image 504. The corresponding feature points among different IR images indicate plural feature points corresponding to a common object (such as the same arm shown in images 502, 504 and 506).

For example, in FIG. 5, the feature points P1-P5 (such as the foresaid first feature points) of the IR image 502 are one to one corresponding to the feature points P1'-P5' (such as the foresaid second feature points) of the IR image 504, the feature point P6 gets no correspondence. According to these corresponding feature points P1-P5 and P1'-P5', the image calibrating module 1044 may respectively construct a maximum visible region 5022 (such as the foresaid first region) covering the feature points P1-P5 and a maximum visible region 5042 (such as the foresaid second region) covering the feature points P1'-P5'.

The maximum visible regions 5022 and 5042 respectively include a principle axis D1 and a principle axis D2. The IR images 502 and 504 may be photographed at different angles of view or different distances, and therefore a skew may exist between the principle axes D1 and D2. The image calibrating module 1044 may produce calibration information based on the skew, wherein the calibration information may include rotating angle of image, displacement of image, and zooming scale of image, etc.; so that the calibration information can be used for transforming the IR image 504 into the IR image 506 (such as the calibrated image).

Referring to FIG. 5, the IR image 506 includes a pattern image of vascular distribution 5060 and a wound image region 5064 (such as the third wound image region). Feature points P1"-P5" of the IR image 506 are coordinate transformed from the aforesaid feature points P1'-P5', wherein the principle axis D2' of the maximum visible region 5062 is aligned with the principle axis D1 so that size or location of the maximum visible region 5062 is substantially identical with size or location of the maximum visible region 5022, thereby completing alignments of those IR images.

Thought shapes of the maximum visible regions 5022, 5042 and 5062 are shown in rectangle, the scope of the disclosure is not limited thereto. In some applications, shape or size of the maximum visible region may be embodied depending on distribution of the feature points. Furthermore, a maximum visible region may include plural principle axes, for example, the maximum visible regions 5022 may include two principle axes which are the two diagonal lines (not shown) of the rectangle.

Figure 6:
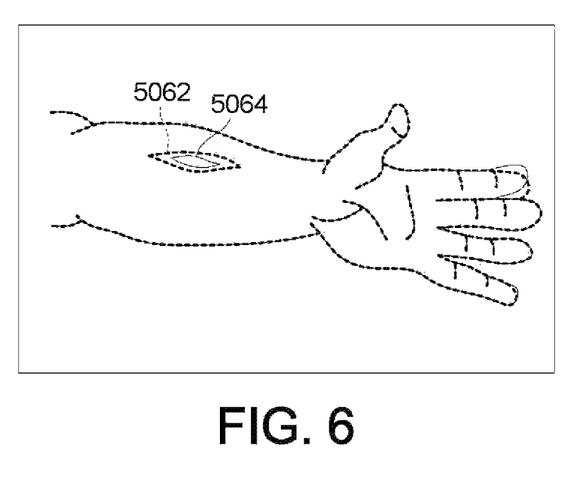
FIG. 6 is a schematic view of change information of a wound status through superposition and alignment of plural IR images according to an embodiment.

FIG. 6 is a schematic view of variations of a wound status through superposition and alignment of plural IR images according to an embodiment. Referring to FIG. 6, the dash-line image 5062 corresponds to the wound image region 5024 of the IR image 502 and the solid-line image 5064 corresponds to the wound image region 5064 of the IR image 506. The wound analyzing module 1046 may compare the wound image region 5024 of the IR image 502 with the wound image region 5064 of the IR image 506 so as to assess area variations of the wound of the arm with time. The wound analyzing module 1046 may further display superposition of the IR image 502 and the IR image 506 for an observer to assess status of the wound.

In summary, the method and the system disclosed in aforementioned embodiments may analyze plural wound images from IR images captured at different time; recognize pattern images of vascular distribution from those IR images for aligning those IR images so as to obtain information of status variations of wound. With the method and the system disclosed in the disclosure, area size of wound may be automatically figured out from those IR images without an additional standard (such as an external-provided scale card), and the IR images captured at different time may be automatically aligned with a reference image without limiting user to capture those IR images at a specific angle of view or a specific distance each time. The aligned images not only make observation for variations of the wound convenient but also improve accuracy for assessing area of the wound.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A system for analyzing wound status, comprising:
    an image obtaining device configured to obtain a plurality of infrared (IR) images which are pictured from a wound of a user's body portion, wherein the plurality of IR images include a first IR image pictured at a first time and a second IR image pictured at a second time, the first IR image includes a first pattern image of vascular distribution of the user's body portion and the second IR image includes a second pattern image of vascular distribution of the user's body portion; and
    an image analyzing device, coupled to the image obtaining device, including:
        a wound detecting module configured to detect a first wound image region from the first IR image, and detects a second wound image region from the second IR image;
        an image calibrating module configured to respectively recognize a non-wound region from the first IR image and a non-wound region from the second IR image to obtain a first feature group and a second feature group, produce calibration information according to the first feature group and the second feature group, and utilize the calibration information for aligning the second IR image to the first IR image to produce a calibrated image; and
        a wound analyzing module configured to recognize a third wound image region from the calibrated image and compares the third wound image region and the first wound image region for finding out variations of the wound.

2. The system of claim 1, wherein the wound detecting module is configured to perform a thresholding process and/or an edge-detecting process on the first IR image and the second IR image, to detect the first wound image region and the second wound image region from the first IR image and the second IR image, respectively.

3. The system of claim 1, wherein the first feature group comprises at least one feature point of a vascular distribution in the first pattern image and the second feature group comprises at least one feature point of a vascular distribution in the second pattern image.

4. The system of claim 1, wherein plural first feature points of the first feature group are one to one corresponding to plural second feature points of the second feature group, and the image calibrating module is configured to analyze a skew between a principle axis of a first region and a principle axis of a second region to produce the calibration information, wherein the first region is an image region covering the plural first feature points and the second region is an image region covering the plural second feature points.

5. The system of claim 4, wherein the image calibrating module is configured to utilizes the calibration information for aligning the second IR image to the first IR image so as to produce the calibrated image.

6. The system of claim 1, wherein the wound analyzing module is configured to calculate difference of feature values of pixels in the first IR image to figure out an area size of the first wound image region and calculate, based on the area size of the first wound image region, an area size of the third wound image region by comparing the third wound image region with the first wound region.

7. The system of claim 1, wherein the first time is different from the second time.

8. The system of claim 1, further comprising an IR light source configured to project IR light to the user's body portion.

9. The system of claim 1, wherein the first IR image is a Top-View IR image pictured from top of the wound.

10. A method for analyzing wound status, comprising:
    obtaining a plurality of infrared (IR) images which are pictured from a wound of a user's body portion, wherein the plurality of IR images include a first IR image pictured at a first time and a second IR image pictured at a second time, the first IR image includes a first pattern image of vascular distribution of the user's body portion and the second IR image includes a second pattern image of vascular distribution of the user's body portion;

detecting a first wound image region and a second wound image region from the first IR image and the second IR image respectively;

respectively recognizing a first non-wound region from the first IR image and a second non-wound region from the second IR image to obtain a first feature group and a second feature group;

producing calibration information according to the first feature group and the second feature group;

utilizing the calibration information for aligning the second IR image to the first IR image to produce a calibrated image; and recognizing a third wound image region from the calibrated image and making comparison between the third wound image region and the first wound image region for finding out variations of the wound.

11. The method of claim 10, further comprising:

performing a thresholding process and/or an edge-detecting process on the first IR image and the second IR image to respectively detect the first wound image region and the second wound image region from the first IR image and the second IR image; and marking the first wound image region and the second wound region for excluding the first wound region and the second wound region from the first IR image and the second IR image, respectively, in the step of obtaining the first feature group and the second feature group.

12. The method of claim 10, wherein the first feature group comprises at least one feature point of a vascular distribution in the first pattern image and the second feature group comprises at least one feature point of a vascular distribution in the second pattern image.

13. The method of claim 10, wherein plural first feature points of the first feature group are one to one corresponding to plural second feature points of the second feature group, and the method further comprises analyzing a skew between a principle axis of a first region and a principle axis of a second region to produce the calibration information, wherein the first region is an image region covering the plural first feature points and the second region is an image region covering the plural second feature points; and aligning the principle axis of the second region to the principle axis of the first region so as to transform the second IR image to the calibrated image.

14. The method of claim 10, further comprising:

calculating difference of feature values of pixels in the first IR image to figure out an area size of the first wound image region; and calculating, based on the area size of the first wound image region, an area size of the third wound image region by comparing the third wound image region with the first wound image region.

15. The method of claim 10, wherein the first time is different from the second time.

* * * * *